(12) United States Patent
Sathe et al.

(10) Patent No.: US 10,836,730 B2
(45) Date of Patent: Nov. 17, 2020

(54) PROCESS FOR PREPARATION AND PURIFICATION OF VORTIOXETINE HYDROBROMIDE

(71) Applicant: Unichem Laboratories Ltd, Maharashtra (IN)

(72) Inventors: Dhananjay G. Sathe, Maharashtra (IN); Arijit Das, Goa (IN); Vishal Kulkarni, Maharashtra (IN); Tushar Patil, Maharashtra (IN); Yogesh Patil, Maharashtra (IN); Prafulla Nagawade, Maharashtra (IN)

(73) Assignee: UNICHEM LABORATORIES LTD., Mumbai (IN)

( * ) Notice: Subject to any disclaimer, the term of this patent is extended or adjusted under 35 U.S.C. 154(b) by 0 days.

(21) Appl. No.: 16/486,315

(22) PCT Filed: Feb. 21, 2018

(86) PCT No.: PCT/IB2018/051054
§ 371 (c)(1),
(2) Date: Aug. 15, 2019

(87) PCT Pub. No.: WO2018/154451
PCT Pub. Date: Aug. 30, 2018

(65) Prior Publication Data
US 2020/0010429 A1 Jan. 9, 2020

(30) Foreign Application Priority Data

Feb. 23, 2017 (IN) .............................. 201721006442

(51) Int. Cl.
*C07D 241/04* (2006.01)
*A61K 31/496* (2006.01)
(52) U.S. Cl.
CPC .......... *C07D 241/04* (2013.01); *A61K 31/496* (2013.01); *C07B 2200/13* (2013.01)

(58) Field of Classification Search
CPC .......................... C07D 295/096; A61K 31/496
USPC ....................................... 544/336; 514/252.12
See application file for complete search history.

(56) References Cited

U.S. PATENT DOCUMENTS

2014/0163043 A1 6/2014 Ruhland et al.

FOREIGN PATENT DOCUMENTS

| WO | WO-2016004908 A1 * | 1/2016 | ........... C07D 211/20 |
|---|---|---|---|
| WO | 2016/079751 A2 | 5/2016 | |
| WO | 2016/125190 A2 | 8/2016 | |

OTHER PUBLICATIONS

Bickak, *Graft Copolymerization of Butyl Acrylate and 2-Ethyl Hexyl Acrylate from Labile Chlorines of Poly(vinyl chloride) by Atom Transfer Radical Polymerization*, Journal of Polymer Science : Part A : Polymer Chemistry, vol. 41, Sep. 24, 2003, pp. 3457-3462 (6 pages).
International Search Report and Written Opinion issued in PCT/IB2018/051054 dated Jun. 1, 2018 (10 pages).

* cited by examiner

*Primary Examiner* — Venkataraman Balasubramanian
(74) *Attorney, Agent, or Firm* — Kilpatrick Townsend & Stockton LLP

(57) ABSTRACT

The present invention is related to an improved process for the preparation and purification of crystalline Vortioxetine hydrobromide of Formula-I. The process according to present invention is operationally simple and suitable for industrial application which will avoid hazardous chemicals and eliminate column chromatography to get ICH quality of pharmaceutically acceptable active pharmaceutical ingredient having snow white appearance.

8 Claims, 1 Drawing Sheet

FIG. 1: X-Ray powder diffraction pattern of crystalline form of Vortioxetine hydrobromide (Formula-I)
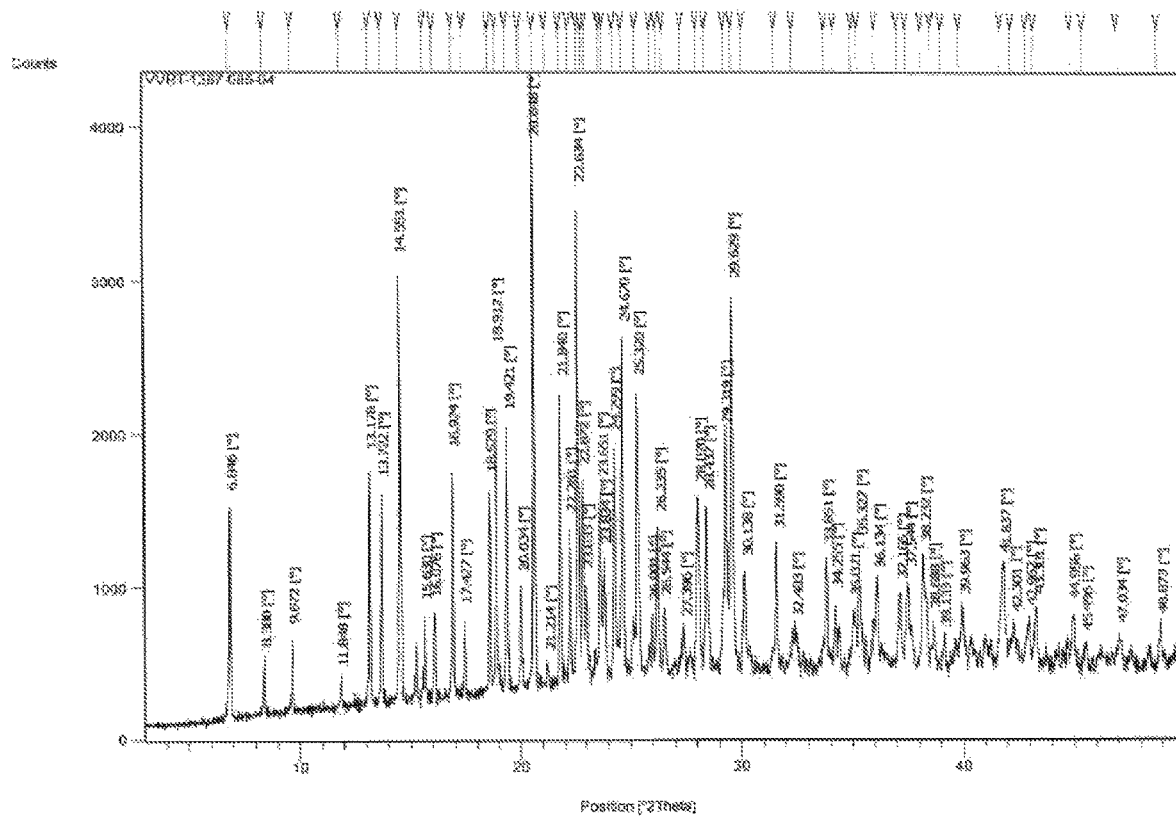

PROCESS FOR PREPARATION AND PURIFICATION OF VORTIOXETINE HYDROBROMIDE

This application is a U.S. National Stage of International Application No. PCT/IB2018/051054, which claims the benefit of priority of IN201721006442 filed on Feb. 23, 2017, the content of which are incorporated herein by reference in their entirety.

FIELD OF INVENTION

The present invention is related to an efficient and improved process for the preparation and purification of Vortioxetine hydrobromide (Formula-I) with high pharmaceutical purity. The present invention also provides novel crystalline form of 1-(2-((2,4-Dimethyl phenylsulfanyl)-phenyl) piperazine hydrobromide (Formula-I). The present invention also provides a process for the preparation of crystalline forms of Vortioxetine hydrobromide (Formula-I).

BACKGROUND OF THE INVENTION

The chemical name for Vortioxetine hydrobromide is 1-[2-(2,4-dimethylphenyl-sulfanyl)phenyl]piperazine hydrobromide. The empirical formula is $C_{18}H_{22}N_2S$. HBr and the molecular weight is 298.45 (free base). Vortioxetine hydrobromide exhibits serotonin reuptake inhibition activity combined with an activity on the serotonin receptor 1A (5-$HT_{1a}$) and the serotonin receptor 3 (5-$HT_3$), developed by Lundbeck and Takeda. In September, 2013, it was approved by the U.S. FDA for the treatment of Major Depressive Disorder (MDD) in adults with the trade name Trintellix.

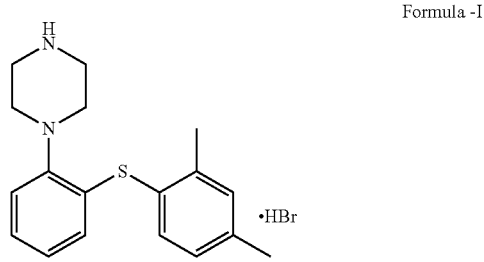 [SMILES: Cc1ccc(Sc2ccccc2N2CCNCC2)c(C)c1 ; Br]

Formula -I

U.S. Pat. No. 7,144,884 teaches a process to prepare Vortioxetine. The process comprises use of solid polystyrene support followed by decomplexation using light irradiation and purification by using preparative LC-MS and ion-exchange chromatography. The overall yield of the reaction is only 17% with 95% purity, which limits its commercial production. The multiple processes are disclosed in the patent to prepare bases analogous to Vortioxetine and their salts.

U.S. Pat. No. 8,722,684 disclosed a process for the synthesis of Vortioxetine hydrobromide of (Formula-) by the condensation of 2,4-dimethylthiophenol and 1,2-dibromobenzene in presence of palladium catalyst and phosphine ligand to get 1-(2-bromophenylsulfanyl)-2,4-dimethylbenzene intermediate. The obtained intermediate optionally isolated, was then condensed using piperazine derivative in presence of palladium catalyst and phosphine ligand to get Vortioxetine hydrobromide. The overall yield of the reaction is only 61% with 95% purity, with preparative HPLC. This patent also includes various polymorph and salt formation.

The process involves use of costly reagents like expensive palladium catalyst and phosphine ligand. According to inventors of this patent application, it is very difficult to make these crystalline forms as similar solvent type is used for the preparation of all the polymorphs.

WO 2015/044963 A1 discloses a new amorphous form of Vortioxetine hydrobromide using water as solvent and the API was isolated using spray drying technique. According to inventors of this application, in this technique there might be a possibility to get hydrated polymorph of Vortioxetine hydrobromide.

US 2015/0266841 discloses a crystalline new polymorph of Vortioxetine hydrobromide form delta using ethanol as a solvent. In this polymorphic form the Vortioxetine hydrobromide generated as a hydrate form.

WO2014/161976 disclosed a process for the preparation of Vortioxetine hydrobromide which comprises;
i. condensation of ortho chloro nitrobenzene (Formula-III) with 2,4-dimethyl thiophenol (Formula-II) in presence of potassium carbonate as a base and dimethyl formamide as a solvent to obtain (2,4-dimethylphenyl)(2-nitrophenyl) sulfane (Formula-IV);
ii. the obtained (2,4-dimethyl phenyl)(2-nitrophenyl)sulfane (Formula-IV) was reduced in presence of Iron and acetic acid to get 2-((2,4-dimethyl phenyl)thio)aniline (Formula-V);
iii. the obtained 2-((2,4-dimethyl phenyl)thio)aniline (Formula-V) was reacted with bis(2-chloroethyl)amine hydrochloride in presence of diethylene glycol methyl ether at 130° C. for three days to get Vortioxetine hydrochloride (Formula-Ia);
iv. Vortioxetine hydrochloride (Formula-Ia) was then basified by using sodium hydroxide followed by salt formation using aq. Hydrobromic acid produced Vortioxetine hydrobromide salt (Formula-Ia).

The reaction sequence is indicated in Scheme-1

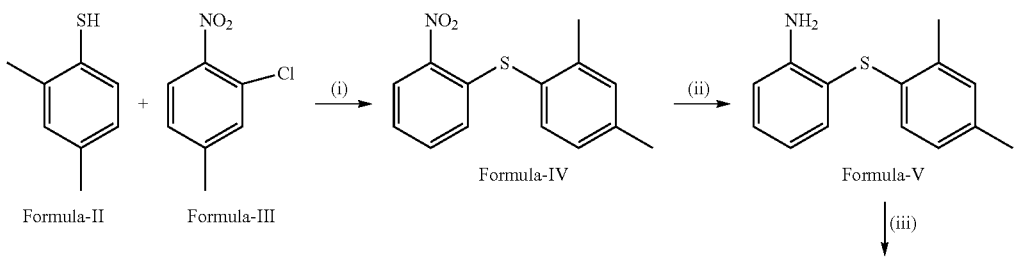

Scheme-1

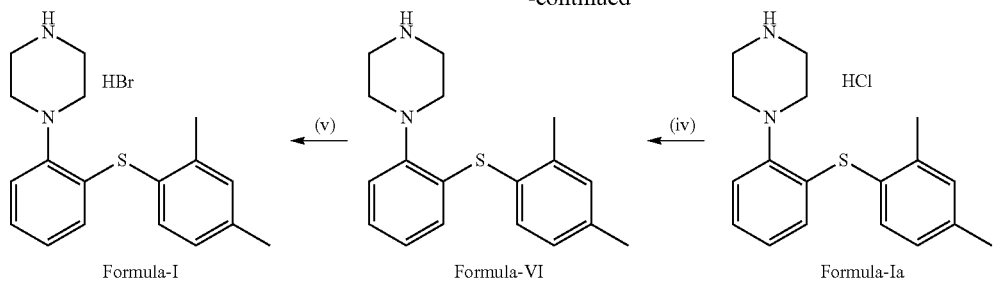

-continued

Formula-I      Formula-VI      Formula-Ia

Reagent: (i) Potassium carbonate, DMF, 25° C., 18 h (ii) Fe, Acetic Acid, 25° C., 16 h (iii) bis(2-chloroethyl)amine hydrochloride, Methylenediglycol, 130° C., 3 days (iv) 1M NaOH Methyl THF, 25° C., 1 h (v) 48% HBr, Isopropyl acetate, 25° C., 1 h.

Scheme-1 suffers from several disadvantages such as poor yield of the overall process (43%), use of longer reaction time such as 3 days at 130° C. which limits its commercial scale production. It is also silent about the purity of vortioxetine hydrobromide.

The process described in the research journal *Synthesis.* 2015. 47, 1387-1389 by Y. Mao et al describes the cyclization of the piperazine ring. The process at 160-170° C. give a light-yellow solution. This process is not reproducible as 1,2-dichlorobenzene in presence of reactants forms a dark brown to tar coloured product.

The processes taught by prior art have complex methodologies and have several drawbacks namely expensive reagents, lower yields, longer duration of reactions and the reactions are less user friendly. These drawbacks limit the commercial exploitation or the large scale applications of the inventions. Considering the drawbacks of prior art and use of complex methodologies for the preparation of the Vortioxetine hydrobromide (Formula-I), there is an urgent and pressing need for simple, energy economical, cheaper, plant friendly and environment friendly process for the preparation and purification of Formula-I, particularly an improved purification process which will give the ICH quality Vortioxetine hydrobromide with higher yield.

OBJECT OF THE INVENTION

The main object of the present invention is to provide an improved process for the preparation and purification of Vortioxetine hydrobromide (Formula-I) which has better overall yield and quality as per ICH guidelines.

Another object of the present invention is to provide an improved process for the synthesis of Vortioxetine hydrobromide (Formula-I) as a pharmaceutically acceptable salt.

Yet another object of the present invention is to provide a process for the preparation of stable polymorph of Vortioxetine hydrobromide, the process comprising;
a) providing a solution of Vortioxetine hydrobromide in one or more organic solvents; and
b) obtaining a stable polymorph of Vortioxetine hydrobromide by the removal of the solvent.

Yet another object of the present invention is to avoid expensive metal catalyst and column chromatography for the preparation of different stages of Vortioxetine hydrobromide (Formula-I).

Yet another object of the invention is to prepare a novel crystal form of Vortioxetine hydrobromide.

Yet another object of the invention is to provide the process to prepare novel crystal form of Vortioxetine hydrobromide, the process comprising;
a) providing a solution of Vortioxetine hydrobromide in one or more organic solvents; and
b) obtaining a stable polymorph of Vortioxetine hydrobromide by the removal of the solvent.

Yet another object of the present invention is to provide a simple process which will avoid stringent requirements like maintaining anhydrous conditions during reaction and can be scaled up easily.

Yet another object of the invention is to provide an effective and industrially advantageous process for purification of Vortioxetine which give snow-white material.

SUMMARY OF THE INVENTION

According to the main object of the present invention, there is provided an improved process for the preparation and purification of Vortioxetine hydrobromide (Formula-I) which has better overall yield and quality as per ICH guidelines and which comprises:
i. condensation of ortho halo (floro, chloro, bromo, iodo) nitrobenzene (Formula-IX) with 2,4-dimethyl thiophenol (Formula-II) in presence of a base and a suitable solvent to get (2,4-dimethyl phenyl)(2-nitrophenyl) sulfane (Formula-IV);
ii. the obtained (2,4-dimethyl phenyl)(2-nitrophenyl) sulfane (Formula-IV) was then reduced in presence of a reducing agent to get 2-((2,4-dimethyl phenyl) thio) aniline (Formula-V);
iii. the obtained product 2-((2,4-dimethyl phenyl) thio) aniline (Formula-V) was then reacted with bis-(2-chloroethyl) amine hydrochloride in presence of 1,2-dichloro benzene at 145-180° C. to get Vortioxetine hydrochloride (Formula-Ia);
iv. optionally isolated Vortioxetine hydrochloride (Formula-Ia) and reacted using aq. Hydrobromic acid followed by isolation and purification using mixture of 2-butanol and water to produce Vortioxetine hydrobromide (Formula-I).

The reaction sequence is indicated in Scheme-2.

Scheme-2

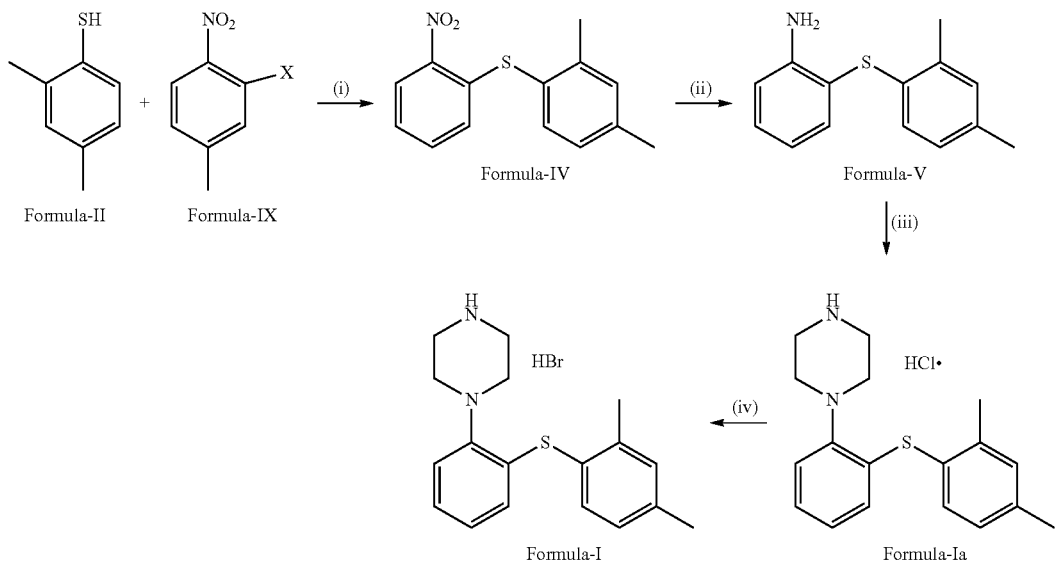

Reagent: (i) Sodium hydroxide, Methanol, 25° C., 8 h (ii) Raney Ni, Methanol: MDC, 25° C. to 45° C., 4 h (iii) bis(2-chloroethyl)amine or bis(2- chloroethyl)amine. HCl 1,2-dichlorobenzene, 165-180° C., 6 h (iv) 48% HBr, 2-butanol, 25° C., 1 h.

By the process disclosed above synthesis of Vortioxetine hydrobromide (Formula-I) as a pharmaceutically acceptable salt is rendered possible. The process also avoids use of column chromatography for preparation of Vortioxetine hydrobromide.

BRIEF DESCRIPTION OF THE FIGURE

FIG. 1: X-Ray powder diffraction pattern of crystalline form of Vortioxetine hydrobromide (Formula-I)

DETAILED DESCRIPTION OF THE INVENTION

There is provided an improved, efficient, process for preparation and purification of a novel crystalline pharmaceutically acceptable Vortioxetine hydrobromide of Formula-I comprising
  i. condensation of ortho halo (fluoro, chloro, bromo, iodo) nitrobenzene (Formula-IX) with 2,4-dimethyl thiophenol (Formula-II) in presence of a base and a suitable solvent to get (2,4-dimethyl phenyl)(2-nitrophenyl) sulfane (Formula-IV);
  ii. the obtained (2,4-dimethyl phenyl)(2-nitrophenyl) sulfane (Formula-IV) was then reduced in presence of a reducing agent to get 2-((2,4-dimethyl phenyl) thio) aniline (Formula-V);
  iii. the obtained product 2-((2,4-dimethyl phenyl) thio) aniline (Formula-V) was then reacted with bis(2-chloroethyl) amine hydrochloride in presence of 1,2-dichloro benzene at 145-180° C. to get Vortioxetine hydrochloride (Formula-Ia);
  iv. optionally isolated Vortioxetine hydrochloride (Formula-Ia) and reacted using aq. Hydrobromic acid followed by isolation and purification using mixture of 2-butanol and water to produce Vortioxetine hydrobromide (Formula-I).

In the present invention the ortho chloro nitrobenzene compound of formula-III and 2,4-dimethyl thiophenol compound of formula-II was obtained from commercially available source and used directly.

The condensation of ortho halogenated nitrobenzene (Formula-IX) such as ortho chloro nitrobenzene of formula-III with 2,4-dimethyl thiophenol (Formula-II) in presence of a base such as sodium hydroxide, potassium hydroxide, potassium carbonate, sodium carbonate and a suitable solvent such as methanol, ethanol, ethyl acetate, isopropyl alcohol at room temperature to get (2,4-dimethyl phenyl)(2-nitrophenyl) sulfane (Formula-IV) The reduction of (2,4-dimethyl phenyl)(2-nitrophenyl) sulfane (Formula-IV) was then carried out using reducing agent such as Raney nickel, palladium in carbon, sodium dithionate at room temperature to get 2-((2,4-dimethyl phenyl) thio) aniline (Formula-V).

The obtained product 2-((2,4-dimethyl phenyl) thio) aniline (formula-V) was then reacted with bis(2-chloroethyl) amine hydrochloride in presence of 1,2-dichloro benzene at 165-170° C. to get Vortioxetine hydrochloride (Formula-Ia). Vortioxetine hydrochloride (Formula-Ia) was then reacted using aqueous (aq.) Hydrobromic acid to produce Vortioxetine hydrobromide (Formula-I), which was purified using 2-butanol or mixture of 2-butanol and water to get the novel crystalline polymorphic form. The product is snow white in appearance.

The reaction scheme for the synthesis of Vortioxetine hydrobromide is shown in Scheme-3.

Scheme-3

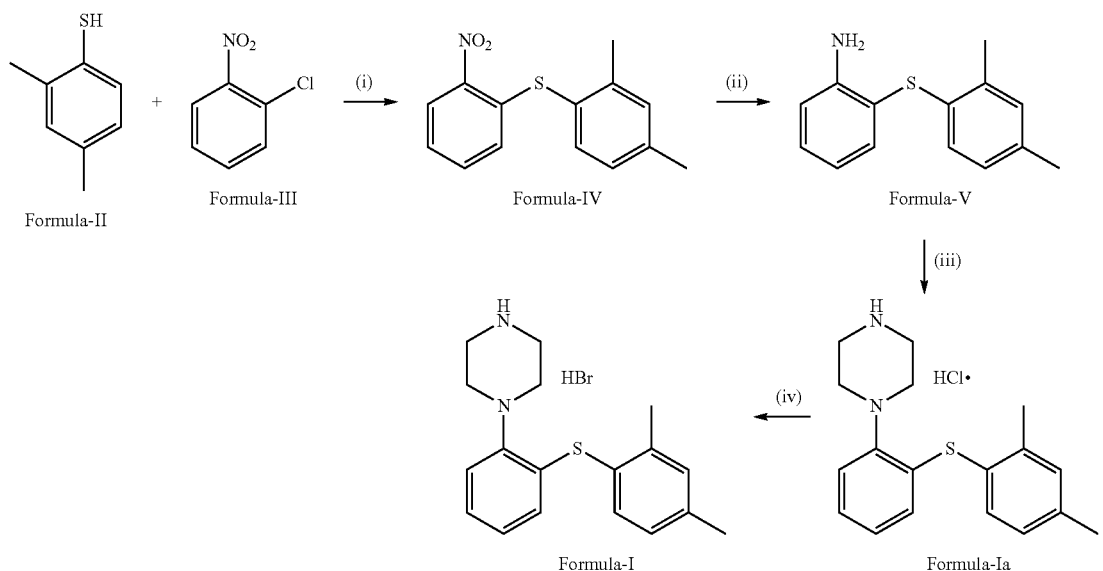

Reagent: (i) Sodium hydroxide, Methanol, 25° C., 6 h (ii) Raney Ni, Methanol:MDC, 25° C. to 45° C., 4 h (iii) bis(2-chloroethyl)amine or bis(2-chloroethyl)amine•HCl, 1,2-dichlorobenzene, 165-180° C., 6 h (iv) 48% HBr, 2-butanol, 25° C., 1 h.

Surprisingly it was found, that the product purified using 2-butanol or 2-butanol/water mixture has ICH quality and has snow white appearance.

One aspect of the present invention is to provide a novel crystalline form of Vortioxetine hydrobromide of Formula-I, which has an X-ray diffraction pattern with peaks at 6.84, 8.38, 9.67, 13.17, 13.72, 14.55, 18.91, 19.42, 20.64, 21.84, 22.63, 22.87, 24.66, 25.32, 29.31, 29.62±0.2 2θ degrees two theta. X-ray diffraction intensity with the diffraction angle 2θ as shown in FIG. 1

The term 'novel crystalline form' is intended to indicate that the crystalline compound which is free of impurities such as intermediates formed in the process of formation of the compound or any other impurity the skilled person may anticipate. Further the compound is snow white in appearance and qualifies all the ICH standards.

These aspects of the present invention substantially increase the inherent utility of the invention.

Thus present invention is novel, non-obvious over prior art and has tremendous utility and industrial application. Prior art is devoid of use of butanol as solvent for purification with specific ratio of water.

Non-obviousness of the invention resides in the fact that whiter or snow white product would be available if 2-butanol with specific ratio of water is used for purification. A process to purify Vortioxetine Hydrobromide using mixture of 2-butanol:water is unheard of. Novelty and inventive step of the invention resides in the process to purify Vortioxetine Hydrobromide wherein the ratio of 2-butanol:water is selected from 1.0:1.0, 1.0:0.75, 1.0:0.50, 1.0:0.25 to 1:0.1, more preferably 1:0.1.

Simpler process is to be understood as a process which will avoid stringent requirements like maintaining anhydrous conditions during reaction and can be scaled up easily.

Quantitative yield as mentioned in the example is to be interpreted as 100% yield.

While the present invention has been described in terms of its specific aspects, certain modifications and equivalents will be apparent to those skilled in the art and are intended to be included within the scope of the present invention.

Following section describes and illustrates the invention by way of examples.

Without limiting the scope of the present invention. Several variants of these examples would be evident to persons ordinarily skilled in the art.

EXAMPLES

Example-1: Preparation of (2,4-dimethylphenyl)(2-nitrophenyl)sulfane (Formula-IV)

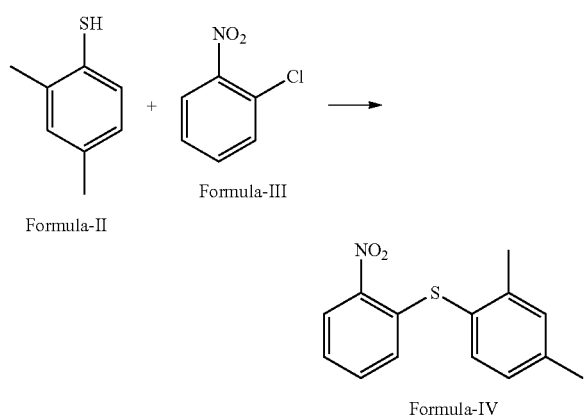

Potassium hydroxide solution (243 g in 900 ml methanol) was added into solution of 2,4-dimethyl thiophenol (300 g) and 2-chloro nitrobenzene (376 g) in methanol (300 ml). The resulting solution was stirred for about 6-8 hours at ambient temperature. Solid were collected by filtration and washing with methanol/water 1:1 (300 ml) to get the title compound with 95% yield and 99% purity by HPLC.

Example-2: Preparation of 2-[(2,4-dimethylphenyl)thio]aniline (Formula-V)

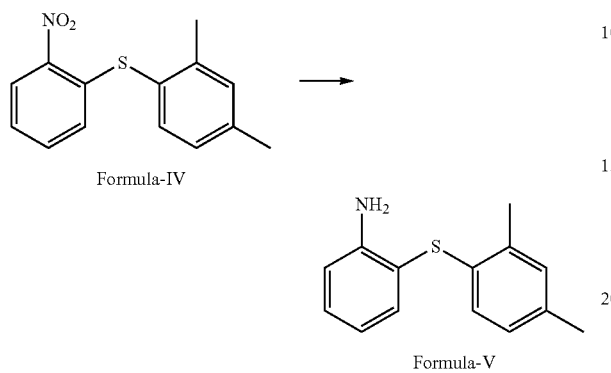

200 g of nitro compound (Formula-IV) from example 1, was stirred in methanol: MDC (7:3) mixture followed by the addition of 20 g (10% w/w) Raney nickel catalyst. Resulting reaction mass was stirred at 45° C. in hydrogen atmosphere. After completion of reaction mass filtered through celite and distilled out under vacuum. Further reaction mass dissolved into MDC and washed with water. Separated out MDC layer, distill out and degas to get title product with quantitative yield and 98% purity by HPLC.

Example-3: 1-[2-(2,4-dimethylphenylsulfanyl)phenyl]piperazine hydrochloride (Formula-Ia)

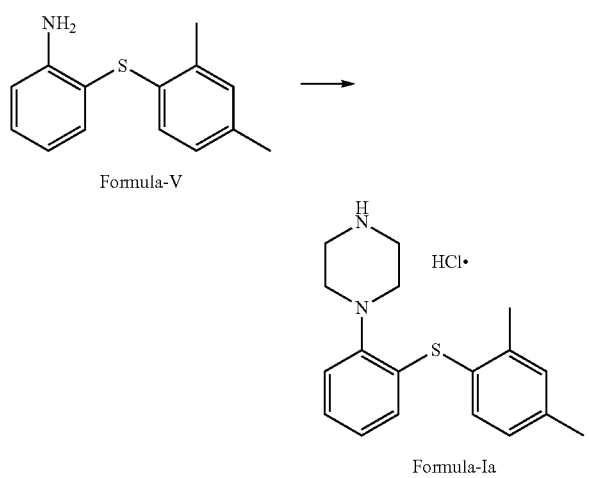

Charge 50 g of amine compound (Formula-V) followed by Bis(2-chloroethyl)-amine.HCl in 1,2-dichlorobenzene (250 ml) at 25-30° C. Raise temperature up to 165-180° C. and maintain the reaction for 6 h. After completion of reaction gradually cool to ambient temperature. Stirred overnight and filtered resulting Formula-Ia with 70% yield and 98% purity by HPLC.

Example-4: 1-[2-(2,4-dimethylphenylsulfanyl)phenyl]piperazine hydrobromide (Formula-I)

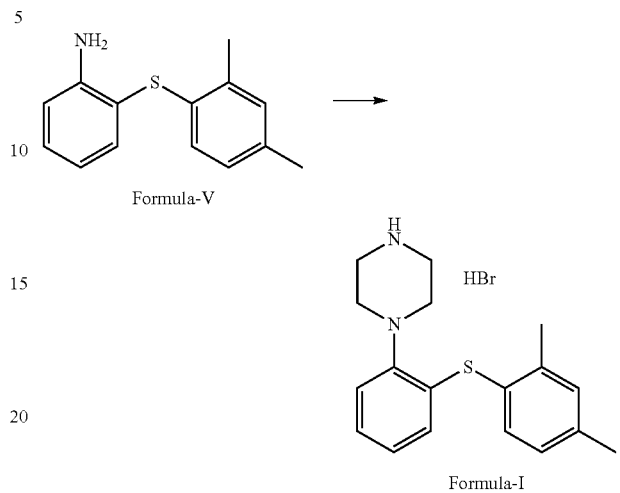

Charge 50 g of amine compound (Formula-V) followed by bis(2-chloroethyl) amine.HCl in 1,2-dichlorobenzene (250 ml) at 25-30° C. Raise temperature up to 145-180° C. and maintain 6-7 hours. After completion of reaction gradually cool to ambient temperature. Charge Aqueous HBr (53 ml) and 2-butanol (250 m), stirred for few hours and filtered resulting Formula-I with 75% yield and 99.95% purity by HPLC.

Example-5: Purification of 1-[2-(2,4-dimethylphenylsulfanyl)phenyl]piperazine hydrobromide (Formula-I) with 2-butanol and Water (1:0.1 Ratio)

Charge Formula-I (50 g) compound into 2-butanol (500 ml) and raise temperature up to 80-85° C. and water added to get clear solution (50 ml). Maintain reaction mass temperature 80-85° C. for an hour and gradually cool to ambient temperature and filtered resulting 85% yield and 99/purity by HPLC. The product has XRPD values as, 6.84, 8.38, 9.67, 13.17, 13.72, 14.55, 18.91, 19.42, 20.64, 21.84, 22.63, 22.87, 24.66, 25.32, 29.31, 29.62±0.2 2θ.

Example-6: Purification of 1-[2-(2,4-dimethylphenylsulfanyl)-phenyl]piperazine hydrobromide (Formula-I) with 2-butanol and Water (1:1 Ratio)

Charge Formula-I (50 g) compound into 2-butanol (500 ml) and raise temperature up to 80-85° C. and water added to get clear solution (500 ml). Maintain reaction mass temperature 80-85° C. for an hour and gradually cool to ambient temperature and filtered resulting Form-1 with 80% yield and 99.97% purity by HPLC. The titled product having XRPD values as, 6.84, 8.38, 9.67, 13.17, 13.72, 14.55, 18.91, 19.42, 20.64, 21.84, 22.63, 22.87, 24.66, 25.32, 29.31, 29.62±0.2 2θ.

Example-7: Purification of 1-[2-(2,4-dimethylphenylsulfanyl)-phenyl]piperazine hydrobromide (Formula-I) with 2-butanol and Water (1:0.5 Ratio)

Charge Formula-I (50 g) compound into 2-butanol (500 ml) and raise temperature up to 80-85° C. and water added to get clear solution (250 ml). Maintain reaction mass temperature 80-85° C. for an hour and gradually cool to ambient temperature and filtered resulting Form-1 with 83% yield and 99.93% purity by HPLC. The titled product having XRPD values as, 6.84, 8.38, 9.67, 13.17, 13.72, 14.55, 18.91, 19.42, 20.64, 21.84, 22.63, 22.87, 24.66, 25.32, 29.31, 29.62±0.2 2θ.

We claim:

1. A process for the preparation of crystalline Vortioxetine hydrobromide of Formula-I comprising:

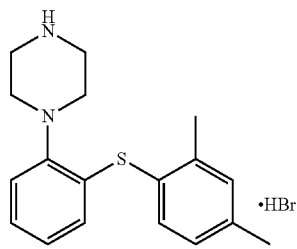

Formula-I i. condens ortho halo nitrobenzene of Formula IX with 2,4-dimethyl thiophenol of Formula-II in presence of a base and a suitable solvent to get (2,4-dimethyl phenyl) (2-nitrophenyl) sulfane of Formula-IV;

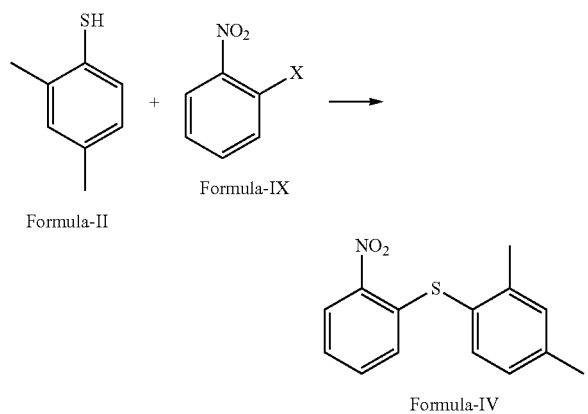

wherein X of Formula-IX is fluoro, chloro, bromo or iodo;

ii. reducing the (2,4-dimethyl phenyl)(2-nitrophenyl) sulfane of Formula-IV in presence of a reducing agent to get 2-((2,4-dimethyl phenyl) thio) aniline of Formula-V;

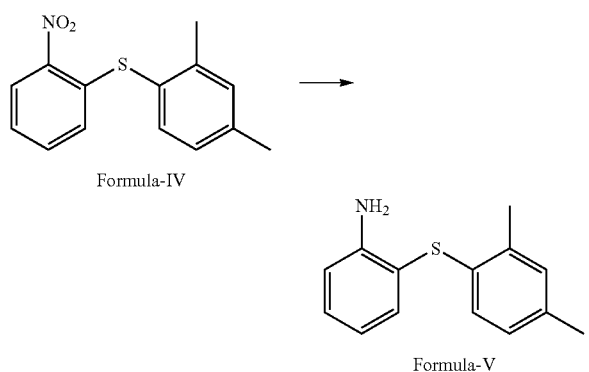

iii. reacting the 2-((2,4-dimethyl phenyl)thio) aniline of Formula-V with bis(2-chloroethyl) amine hydrochloride in presence of 1,2-dichloro benzene at 145-180° C. to get Vortioxetine hydrochloride of Formula-Ia;

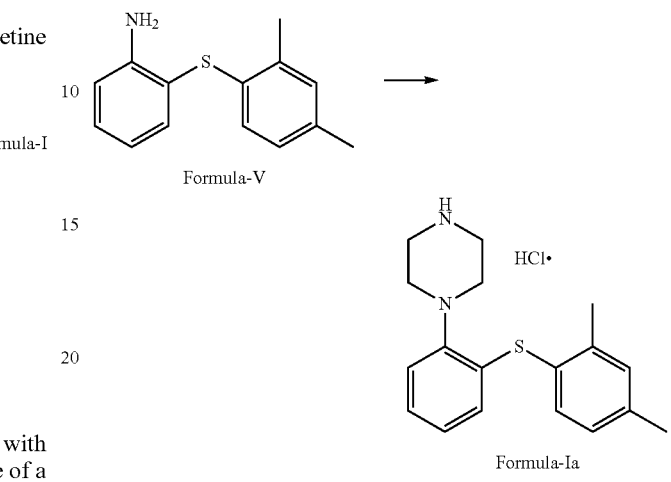

iv. reacting the Vortioxetine hydrochloride of Formula-Ia with aqueous hydrobromic acid to obtain Vortioxetine hydrobrormide of Formula I followed by purification of the Vortioxetine hydrobromide of Formula I using a mixture of 2-butanol and water to obtain a crystalline Vortioxetine hydrobromide of Formula-I.

2. The process as claimed in claim 1, wherein the crystalline Vortioxetine hydrobromide of Formula-I has an X-ray diffraction (XRPD) pattern with peaks at 6.84, 8.38, 9.67, 13.17, 13.72, 14.55, 18.91, 19.42, 20.64, 21.84, 22.63, 22.87, 24.66, 25.32, 29.31, and 29.62 2θ±0.2°.

3. The process as claimed in claim 1, wherein the Vortioxetine hydrochloride of Formula-Ia obtained in step iii is crystalline.

4. The process as claimed in claim 1, wherein the crystalline Vortioxetine hydrobromide of Formula I obtained in step iv comprises impurity of (2,4-dimethyl phenyl)(2-nitrophenyl) sulfane (formula-IV) and 2-((2,4-dimethyl phenyl) thio) aniline (formula-V) not more than 75 ppm.

5. A process to purify Vortioxetine Hydrobromide using a mixture of 2-butanol and water, wherein a ratio of 2-butanol to water is selected from the group consisting of 1:1, 1:0.75, 1:0.5, 1:0.25 and 1:0.1; wherein the Vortioxetine Hydrobromide has an X-ray diffraction (XRPD) pattern with perks at 6.84, 8.38, 9.67, 13.17, 13.72, 14.55, 18.91, 19.42, 20.64, 21.84, 22.63, 22.87, 24.66, 25.32, 29.31, and 29.62 2θ±0.2°.

6. Vortioxetine Hydrobromide purified from a mixture of 2-butanol and water, wherein a ratio of 2-butanol to water is selected from the group consisting of 1:1, 1:0.75, 1:0.5, 1:0.25 and 1:0.1; wherein the Vortioxetine Hydrobromide has an X-ray diffraction (XRPD) pattern with perks at 6.84, 8.38, 9.67, 13.17, 13.72, 14.55, 18.91, 19.42, 20.64, 21.84, 22.63, 22.87, 24.66, 25.32, 29.31, and 29.62 2θ±0.2°.

7. A process for the preparation of Vortioxetine hydrobromide of Formula I comprising:

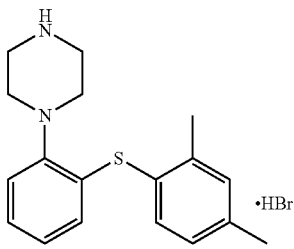

Formula-I

·HBr reacting 2-((2,4-dimethyl phenyl) thio) aniline of Formula-V with bis(2-chloroethyl) amine hydrochloride in presence of 1,2-dichloro benzene at 145-180° C. to obtain Vortioxetine hydrochloride of Formula-Ia;

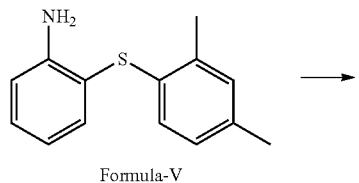

Formula-V

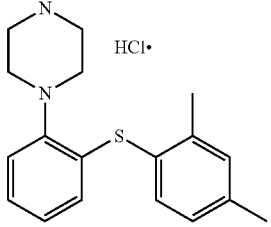

HCl·

Formula-Ia reacting the Vortioxetine hydrochloride of Formula-Ia with aqueous hydrobromic acid to produce Vortioxetine hydrobromide of Formula I followed by purification of the Vortioxetine hydrobromide of Formula I using a mixture of 2-butanol and water to obtain crystalline Vortioxetine hydrobromide of Formula-I, wherein a ratio of 2-butanol to water is selected from the group consisting of 1:1, 1:0.75, 1:0.5, 1:0.25 and 1:0.1.

8. The process as claimed in claim 7, wherein the crystalline Vortioxetine hydrobromide of Formula I comprises impurity of (2,4-dimethyl phenyl)(2-nitrophenyl) sulfane (formula-IV) and 2-((2,4-dimethyl phenyl) thio) aniline (formula-V) not more than 75 ppm.

* * * * *